(12) United States Patent
Mansour et al.

(10) Patent No.: US 8,888,758 B2
(45) Date of Patent: Nov. 18, 2014

(54) CLOSED MALE LUER DEVICE FOR MINIMIZING LEAKAGE DURING CONNECTION AND DISCONNECTION

(75) Inventors: George Michel Mansour, Pomona, CA (US); Tim L. Truitt, Orange, CA (US); Matthew P. Fried, Ontario, CA (US)

(73) Assignee: Carefusion 303, Inc., San Diego, CA (US)

( * ) Notice: Subject to any disclaimer, the term of this patent is extended or adjusted under 35 U.S.C. 154(b) by 44 days.

(21) Appl. No.: 12/204,962

(22) Filed: Sep. 5, 2008

(65) Prior Publication Data

US 2010/0063482 A1    Mar. 11, 2010

(51) Int. Cl.
*A61M 25/18*    (2006.01)
*A61M 39/26*    (2006.01)
*A61M 39/10*    (2006.01)

(52) U.S. Cl.
CPC ....... *A61M 39/26* (2013.01); *A61M 2039/1077* (2013.01); *A61M 2039/1066* (2013.01); *A61M 2039/1033* (2013.01); *A61M 2039/262* (2013.01)
USPC .......................................... 604/539; 604/533

(58) Field of Classification Search
USPC ........... 604/523, 254, 29, 500, 533, 534, 535, 604/536
See application file for complete search history.

(56) References Cited

U.S. PATENT DOCUMENTS

| | | | |
|---|---|---|---|
| 5,569,235 A | 10/1996 | Ross et al. | |
| 7,195,616 B2 | 3/2007 | Diller et al. | |
| 7,329,249 B2 | 2/2008 | Bonaldo | |
| 2003/0032940 A1 | 2/2003 | Doyle | |
| 2003/0060804 A1 | 3/2003 | Vaillancourt | |
| 2004/0217315 A1* | 11/2004 | Doyle | 251/149.1 |
| 2004/0227120 A1 | 11/2004 | Raybuck | |
| 2005/0015075 A1* | 1/2005 | Wright et al. | 604/535 |
| 2005/0228362 A1 | 10/2005 | Vaillancourt | |
| 2006/0118749 A1 | 6/2006 | Ryan et al. | |
| 2006/0192164 A1 | 8/2006 | Korogi et al. | |
| 2006/0208210 A1* | 9/2006 | Raybuck | 251/149.1 |
| 2007/0021721 A1 | 1/2007 | Lopez | |
| 2007/0073270 A1 | 3/2007 | Christensen et al. | |
| 2007/0083162 A1 | 4/2007 | O'reagan et al. | |
| 2007/0088292 A1 | 4/2007 | Fangrow | |
| 2007/0088293 A1 | 4/2007 | Fangrow | |
| 2007/0088294 A1 | 4/2007 | Fangrow | |

(Continued)

FOREIGN PATENT DOCUMENTS

WO    WO 0020070       4/2000
WO    WO 2006062912    6/2006

*Primary Examiner* — Quynh-Nhu H Vu
*Assistant Examiner* — Brandy S Lee
(74) *Attorney, Agent, or Firm* — McDermott Will & Emery LLP

(57) ABSTRACT

A medical connector for minimizing leakage of fluids during connection and disconnection is described. The medical connector includes a body having an inlet port, at least one outlet port adjacent to a male luer portion of the body, and a fluid path between the inlet port and the at least one outlet ports. A retractable seal adjacent to the male luer portion of the body and blocks the outlet ports of the body when the male luer portion of the medical connect is in a disconnected state. The retractable seal is positioned on the body such that it is moved away from the outlet ports upon insertion of the male luer portion of the medical connector into a medical access device thereby unblocking the outlet ports and creating a fluid path through the medical connector.

12 Claims, 4 Drawing Sheets

(56) References Cited

U.S. PATENT DOCUMENTS

| | | |
|---|---|---|
| 2007/0088324 A1 | 4/2007 | Fangrow |
| 2007/0088325 A1* | 4/2007 | Fangrow, Jr. .................. 604/533 |
| 2007/0106244 A1 | 5/2007 | Mosler et al. |

* cited by examiner

CLOSED MALE LUER DEVICE FOR MINIMIZING LEAKAGE DURING CONNECTION AND DISCONNECTION

TECHNICAL FIELD

The present invention relates to medical connectors used in fluid delivery applications, and more specifically to connectors that minimize fluid leakage during connection and disconnection.

BACKGROUND OF THE INVENTION

Medical connections are widely used in fluid delivery systems such as those used in connection with intravenous fluid lines, blood access, hemodialysis, peritoneal dialysis, enteral feeding, drug vial access, etc. Many prior art aseptic medical connections has been to puncture an elastomeric diaphragm or septum, which has one side in contact with the fluid, with a sharpened hollow hypodermic needle. The use of such hypodermic needles has been gradually decreasing as a result of both safety and cost considerations associated with infectious disease acquired from needle sticks. These connectors have been replaced with luer activated connectors which don't require hypodermic needles, but instead use an activator such as a luer on the end of a syringe or IV line to create a fluid path though a valve in a connector. The removal of the connector causes the valve to close when the line is disconnected. Such a system is described in U.S. Pat. No. 5,569,235 to Ross et al.

Typical connectors and valves of this type, such as described by Ross, have many attributes that are not ideal in medical applications for delivery of fluids that could be harmful if contacted by the health care provider or the patient other than through the patient's intravenous ("IV") connection. Oncology drugs such as chemotherapy are examples of fluids that while beneficial to the patient as part of a treatment regimen could be extremely harmful to the health care provider if the chemotherapy drug were to come into contact with the skin of the health care provider or patient.

Traditional medical connectors require the health care provider to exercise great care on connection or disconnection due to the likelihood of the drug remaining inside the connector or dripping, particularly on disconnection when the connectors are primed with fluid. Some female connectors are designed to push fluid in the throat of the connector to the surface during disconnection. While this is desirable for aseptic connectors to provide a swabbable surface, it can result in fluid drips from the device on disconnection. Other connectors use a membrane with a septum that can also allow fluids to escape the connector.

What is needed is a connector for medical fluids that has standardized connections for use with existing medical connectors and also minimizes or eliminates drips on connection or disconnection

BRIEF SUMMARY OF THE INVENTION

Embodiments of the concepts described herein describe a medical connector and method for minimizing fluid leakage, the medical connector and method including a body having an inlet port, at least one outlet port adjacent to a male luer portion of the body, and a fluid path between the inlet port and the at least one outlet ports. A retractable seal is adjacent to the male luer portion of the body to block the outlet ports of the body when the male luer portion of the medical connect is in a disconnected state. The retractable seal is positioned on the body such that it is moved away from the outlet ports upon insertion of the male luer portion of the medical connector into a medical access device thereby unblocking the outlet ports and creating a fluid path through the medical connector.

In other embodiments a medical connector is described for connecting to a medical access device, the connector including a body having an inlet port, at least one outlet port adjacent to a male luer portion of the body, and a fluid path between the inlet port and the at least one outlet ports, and a flexible sleeve fitted over the male luer portion of the body and fixed to the body at an end distal from the outlet ports. The flexible sleeve includes a seal ring proximal to the outlet ports of the body and is operable to seal the outlet ports when the flexible sleeve is in an extended state. The flexible sleeve is positioned to be compressed when the male luer portion of the body is inserted into the medical access device. The compression causes the seal ring to be moved away from the outlet ports along the male luer portion of the body thereby unsealing the outlet ports and creating a fluid path through the connector.

In another embodiment a method of connecting a connector and an access device to create fluid path for medical fluids is described. The method includes inserting a male luer portion of the connector into a female luer portion of the access device and causing a seal blocking outlet ports in the male luer portion of the connector to be retracted from the outlet ports. The method further includes creating a fluid path through the connectors when the male luer portion of the connector has been inserted sufficiently into the access device to create a fluid path from the connector through the outlet ports into the access device, and causing the seal to reseal the outlet ports upon removal of the male luer portion of the connector from the female luer portion of the access device.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
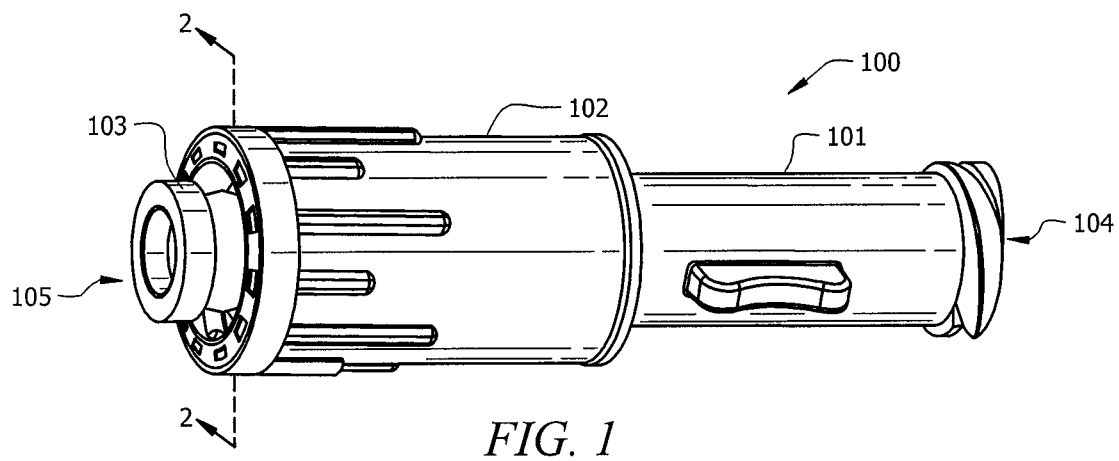
FIG. 1 is a perspective view of an embodiment of a male luer medical connector for fluid delivery according to the concepts described herein.

Referring now to FIG. 1, an embodiment of a medical connector 100 in accordance with the concepts described herein is shown. Medical connector 100 operates as a spin lock luer having a body 101 and a spin lock portion 102. The male luer body is ISO 594-2 compliant and interfaces with standard needless access devices. Medical connector 100 differs from traditional spin lock luer by the inclusion of a retractable elastic sleeve 103 over male luer portion 105 at the distal end of medical connector 100. The proximal end of medical connector 100 includes an inlet port 104 that can be connected to fluid delivery sources or devices such as IV fluid bags, pumps or the like.

As with traditional needleless medical connectors, male luer portion 105 of medical connector 100 is inserted into the female luer of another needleless access device to create a fluid path between a fluid delivery mechanism and a patient. In order to avoid drips and leakage of medical fluids that may be harmful to health care providers or patients, medical connector 100 is designed to minimize or eliminate fluid drips or leakage upon connection of medical connector 100 with another access device, or particularly upon disconnection from another access device with both devices are primed with fluid.

Figure 2:
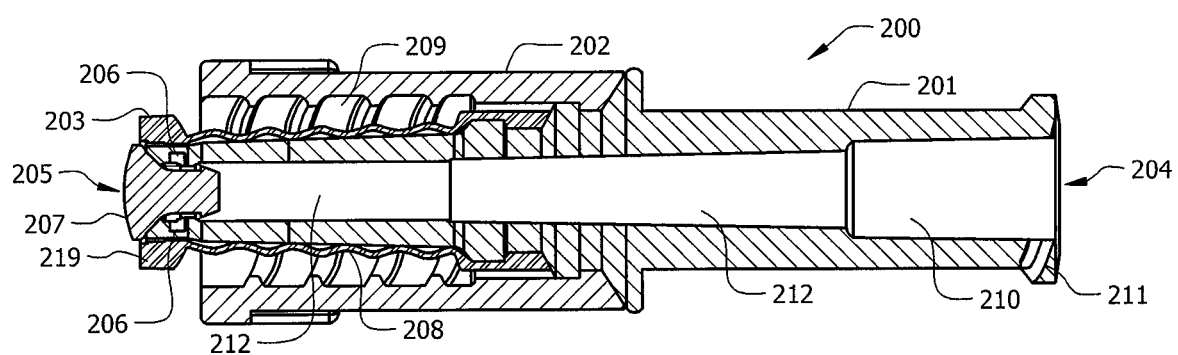
FIG. 2 is a sectional view of the male luer medical connector shown in FIG. 1.

Referring now to FIG. 2, the medical connector from FIG. 1 is shown in a sectional view. As described, medical connector 200 includes body 201. Body 201 has an inlet port 204 adjacent to a threads 211 which allow connector 201 to be securely attached to other access devices. Inlet connection 210, which is shown here as a female luer connector that accepts the male luer of another needleless access devices and allows fluids to pass into fluid path 212. While connector 200 is shown as having a female luer type connector, any type of inlet port could be used, such as a bond pocket or other connector, while remaining within the scope of the concepts described herein. Fluid path 212 communicates with outlet ports 206 in male luer portion 205 of connector 200. Unlike other similar medical connectors in which the fluid path is directly out the end of the male luer, outlet ports 206 are channels in the sides of male luer portion 205 of body 201 and the tip of male luer portion 205 is closed. In embodiments of the medical connector according to the concepts described herein the tip of male luer portion 205 may include a squeegee tip 207, the function of which will be described with reference to FIG. 4. Spin lock portion 202 surrounds the distal end of body 201 and includes inner chamber 209 which has threads for connecting medical connector 200 to other access devices.

Also surrounding male luer portion 205 of body 201 inside chamber 209 of spin lock portion 202 is flexible sleeve 203. Flexible sleeve 203 includes seal ring 219 at its distal end which operates to block outlet ports 206 when flexible sleeve 203 is in its extended position as shown in FIG. 2. As will be discussed, flexible sleeve 203 can be pushed back into chamber 209 unblocking outlet ports 206 and completing the fluid path 212 through connector 200. In embodiments of flexible sleeve 203, sleeve portion 208 can be formed in an accordion shape to allow sleeve portion 208 to bunch together as seal ring 219 is pushed into chamber 209 by the engagement of connector 200 to another access device.

Figure 3A:
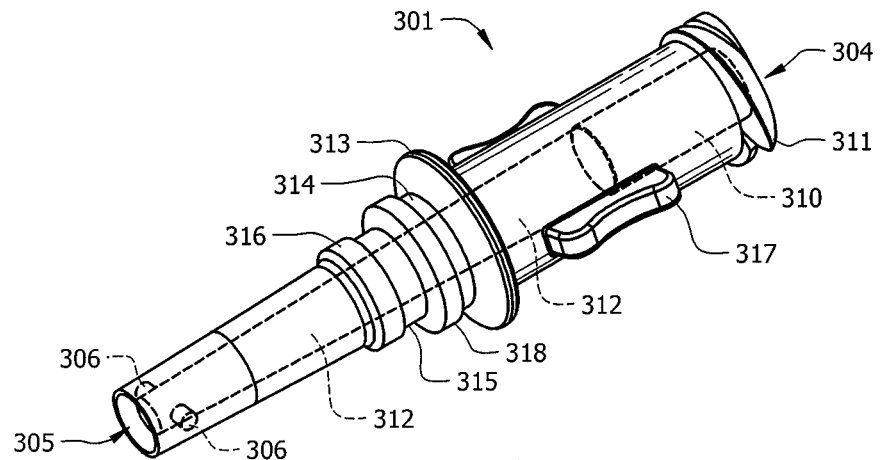
FIGS. 3A-3C are perspective views of embodiments of the components of the male luer medical connector shown in FIG. 1.
Figure 3B:
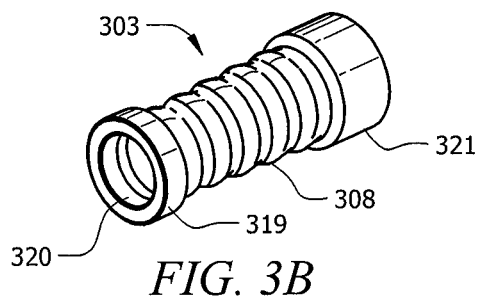
Figure 3C:
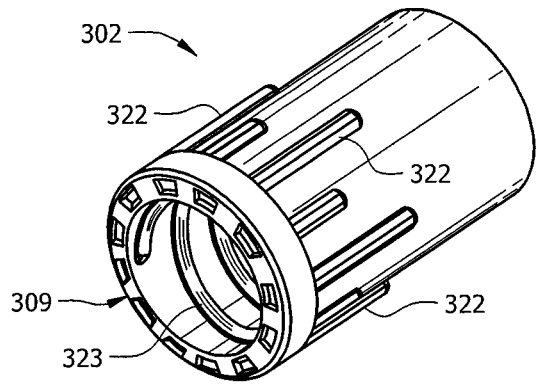

Referring now to FIGS. 3A, 3B and 3C embodiments of the body, flexible sleeve and spin lock portion, respectively, of a medical connector according to the concepts describe herein are shown. FIG. 3A shows an embodiment of body 301. As described, body 301 includes inlet port 304 having connection mechanism 310, outlet ports 306, fluid path 312 and male luer portion 305. Threads 311 or other connection mechanisms can be placed at the proximal end of body 301 adjacent to inlet port 304. Grips 317 are used to facilitate manipulation of body 301 by health care personnel. Plate 313 works with flange 318 and groove 314 to hold spin lock portion 302 while allowing it to spin with respect to body 301. A flange in spin lock portion 302 fits snaps into groove 314 and spin lock portion is held in place by plate 313 and flange 318.

Similarly, flange 318, groove 315 and flange 316 are used to hold flexible sleeve 303 in position relative to body 301. Another flange inside end 321 of flexible sleeve 303 fits into groove 315 and is held in place by flanges 318 and 315, thereby holding flexible sleeve 303 in place. While flange and groove arrangements have been shown to attach spin lock portion 302 and flexible sleeve 303 to body 301, one skilled in the art would recognize that any number of arrangements could be employed to connect the various parts while still being within the scope of the concepts described herein. For example, adhesives, locking hubs, friction fittings or other connection mechanisms could be used to assemble the individual elements into a finished medical connector. Body 301 is preferably formed from polycarbonate plastic but could be formed from any number of materials appropriate for medical connectors.

An embodiment of flexible sleeve 303 is shown in FIG. 3B. Flexible sleeve 303 includes end 321 which provides the attachment to body 301, sleeve portion 308 and seal ring 319. Inner surface 320 of seal ring 319 blocks outlet ports 306 of body 301 when flexible sleeve 303 is in its extended position. Seal ring 319 of flexible sleeve 303 may be pushed toward end 321 as will be described with reference to FIG. 4B causing flexible sleeve 303 to shorten or compress along sleeve portion 308. Sleeve portion 308 may be formed in an accordion shape to allow sleeve portion 308 to bunch together or fold up as flexible sleeve 303 is compressed, or sleeve portion 308 may be merely formed of a compressible material, or otherwise formed or shaped to allow compression and shortening of sleeve portion 308.

As flexible sleeve 303 is shortened, inner surface 320 of seal ring 319 is moved away from outlet ports 306 causing them to be unblock and thereby opening a flow path through body 301. Since embodiments of male luer portion 305 of body 301 may be tapered, the inner diameter of flexible may need to be tapered as well to ensure that inner surface 320 is tight enough against outlet ports 306 to prevent fluid from escaping. Because of this taper, seal ring 319 and sleeve portion 308 should be able to expand as flexible sleeve 303 is compressed. This expansion or stretching of flexible sleeve 303 has the benefit of aiding in the return of flexible sleeve 303 to the extended position when the compression force to seal ring 309 is removed. Flexible sleeve 303 is preferably made from medical grade silicon, but can be made from any material that has the characteristics described with respect to flexible sleeve 303.

Spin lock portion 302 is designed to snap over body 301 as described above. Spin lock portion includes chamber 309 which holds male luer portion 305 of body 301 and flexible sleeve 303. Threads 323 on the inner surface of chamber 309 allow for secure connection to other threaded medical access devices. Grip rails 322 allow spin lock portion 302 to be firmly gripped by health care personnel during twisting motions required to thread or unthread spin lock portion 302 onto or off of another medical access device.

Figure 4A:
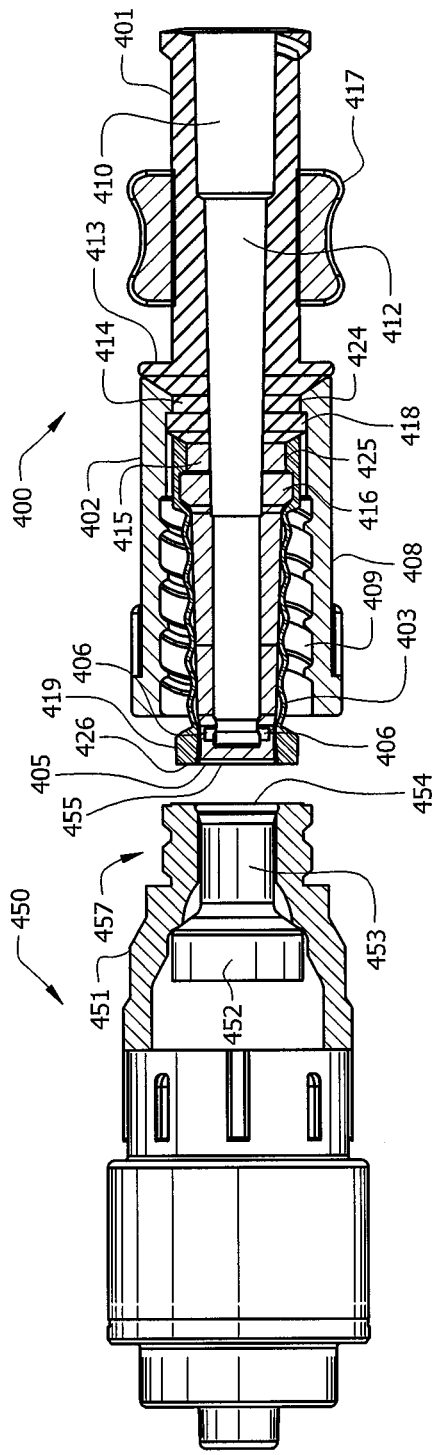
FIGS. 4A and 4B are sectional views of an embodiment of a male luer medical connector in accordance with the concepts shown herein and a deformable valve plug type medical connector in a disconnected state and a connected state respectively.
Figure 4B:
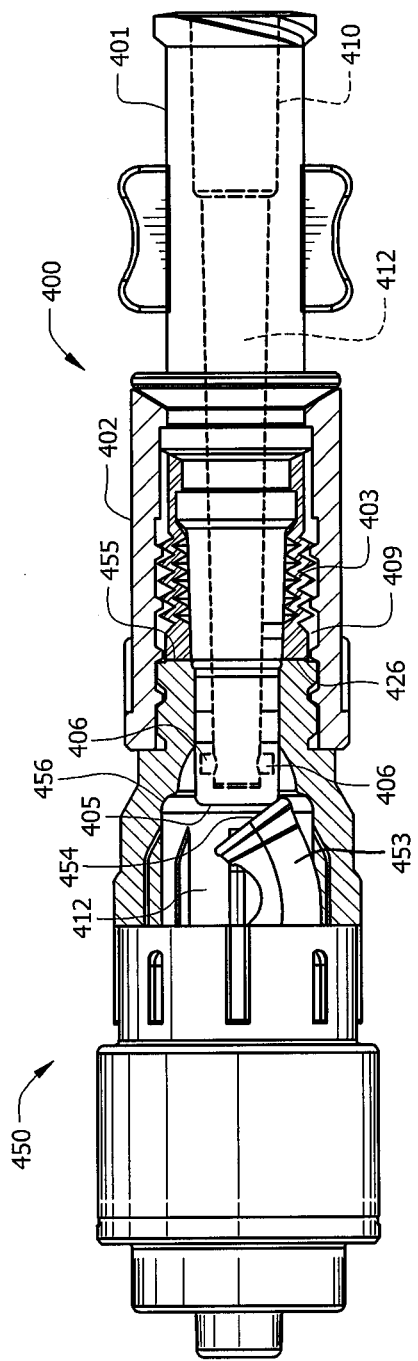

Referring now to FIGS. 4A and 4B, an embodiment of a medical connector 400 is shown in relation to another medical access device 450 to illustrate the operation of connector 400. FIG. 4A shows connector 400 disengaged from medical access device 450 while FIG. 4B shows connector 400 engaged with medical access device 450, creating a fluid path therethrough. Reference will be made to FIGS. 4A and 4B interchangeably as the operation of connector 400 is described.

Connector 400 includes body 401 having an inlet connection mechanism 410, spin lock portion 402 and flexible sleeve 403 as described above. Spin lock portion 402 is secured to body 401 by fitting spin lock flange 424 into groove 414 on body 401. Flange 418 and plate 413 hold spin lock portion 402 in place while allowing spin lock portion 402 to spin freely in relation to body 401. Flexible sleeve 403 has its distal end held in place on body 401 by flange 425 engaging with groove 415 and held in place by flange 416 on body 401. As described, seal ring 419 of flexible sleeve is positioned to block outlet ports 406 in male luer 405 of connector 400.

As can be seen in FIG. 4A, when connector 400 is aligned with medical access device 401, surface 426 of seal ring 419 aligns to engage surface 455 of the female luer portion 457 of device 450. Further, mail luer portion 405 of connector 400 aligns with surface 454 of valve plug 453. FIG. 4B show connector 400 engaged with device 450. In the engaged state, contact between surface 426 of flexible sleeve 403 and surface 455 of device 450 causes flexible sleeve to be compressed into chamber 409 formed by spin lock portion 402.

In the embodiment of flexible sleeve 403 shown, sleeve portion 408 folds along accordion bends, though other mechanisms to control the compression are well within the scope of the concepts described herein. As flexible sleeve 403 is compressed, it no longer blocks outlet valves 406. However, outlet valves 406 are then blocked by the inner surface of throat of female luer portion 457 of device 450.

As male luer portion 405 of connector 400 continues to be inserted into device 450, valve plug 453 compresses into device 450 and the tip of male luer portion 405 reaches chamber 456 where outlet ports 406 are no longer blocked and flow path 412 through connector 400 and medical access device 450 is completed. Connector 400 and device 450 may be securely attached using threads on spin lock portion 402 of connector 400 and threads on female luer portion 457 of device 450.

Upon disconnection, removing connector 400 from device 450 causes outlet ports 406 to again be blocked by the inner surface of the throat of female luer portion 457. This interrupts the fluid path 412 and stops the flow of fluid through connector 400. As connector 400 is disengaged, flexible sleeve 403 extends along male luer portion 405 and as outlet ports 406 are removed from device 450, they are immediately blocked by seal ring 419. A squeegee tip 207 from FIG. 2 can be used to draw excess fluid from the throat of device 450 into the space between flexible sleeve 403 and male luer portion 405 as connector 400 is withdrawn. Even without the squeegee tip, the only fluid that should be released during disconnection would be that fluid trapped in the throat of device 450 as plug 453 extends to seal device 450.

While access device 450 is shown as having a valve plug arrangement, connector 400 will work with any standard female luer of a medical access device including bellows type plugs, devices with septums, or other configurations designed to accept standardized male luer connectors.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A medical connector comprising:
   a body having an inlet port, at least one outlet port in a sidewall of a male luer portion of the body, and a fluid path between the inlet port and the at least one outlet port;
   a flexible sleeve over the sides, but not the tip of the male luer portion of the body, and blocking the at least one outlet port of the body when the male luer portion of the medical connector is in a disconnected state, wherein the flexible sleeve compresses along the male luer portion upon insertion of the male luer portion of the medical connector into a medical access device thereby unblocking the at least one outlet port and creating a fluid path through the medical connector; and
   a squeegee tip fixed to an end of the male luer portion proximal to the at least one outlet port, wherein the squeegee tip removes excess fluid from the medical access device and causes the excess fluid to be trapped in the medical connector by a retractable seal ring coupled to the flexible sleeve.

2. The medical connector of claim 1 further comprising a spin lock attached to the body, the spin lock including threads for attachment to the medical access device.

3. The medical connector of claim 1 wherein the flexible sleeve is fixed to an end of the male luer portion of the body distal from the at least one outlet port.

4. The medical connector of claim 1 wherein the retractable seal is attached to a distal end of the flexible sleeve and the excess fluid is trapped between the flexible sleeve and the male luer portion of the body.

5. A medical connector for connecting to a medical access device, the connector comprising:
   a body having an inlet port, at least one outlet port in a sidewall of a male luer portion of the body, and a fluid path between the inlet port and the at least one outlet port;
   a flexible sleeve fitted over the sides but not the tip of the male luer portion of the body and fixed to the body at an end distal from the at least one outlet port, the flexible sleeve including a seal ring proximal to the at least one outlet port of the body and operable to seal the at least one outlet port when the flexible sleeve is in an extended state, and wherein the flexible sleeve is positioned to be compressed when the male luer portion of the body is inserted into the medical access device, the compression causing the seal ring to be moved away from the at least one outlet port along the male luer portion of the body thereby unsealing the at least one outlet port and creating a fluid path through the connector;

a spin lock attached to the body, the spin lock including threads for attachment to the medical access device; and a squeegee tip fixed to an end of the male luer portion proximal to the at least one outlet port.

6. The medical connector of claim 5 wherein the squeegee tip removes excess fluid from the medical access device and causes the excess fluid to be trapped in the medical connector by the retractable seal.

7. The medical connector of claim 6 wherein the retractable seal is part of a flexible sleeve surrounding the male luer portion of the body and fixed to an end of the male luer portion of the body distal from the at least one outlet port and the excess fluid is trapped between the flexible sleeve and the male luer portion of the body.

8. A method of connecting a connector and an access device to create fluid path for medical fluids, the method comprising:

inserting a male luer portion of the connector into a female luer portion of the access device, wherein the connector includes a squeegee tip fixed to an end of the male luer portion proximal to the at least one outlet port;

compressing a flexible sleeve surrounding the sides but not the tip of the male luer portion, thereby causing a seal portion of the flexible sleeve blocking at least one outlet port in a sidewall of the male luer portion of the connector to be retracted from the at least one outlet port;

creating a fluid path through the connectors when the male luer portion of the connector has been inserted sufficiently into the access device to create a fluid path from the connector through the at least one outlet port into the access device;

causing the seal to reseal the at least one outlet port upon removal of the male luer portion of the connector from the female luer portion of the access device.

9. The method of claim 8 wherein the retractable seal is part of a flexible sleeve surrounding the male luer portion of the body and fixed to an end of the male luer portion of the body distal from the at least one outlet port.

10. The method of claim 9 wherein causing the seal to be retracted includes compressing the flexible sleeve along the male luer portion upon insertion into the medical access device.

11. The method of claim 8 further comprising removing excess fluid from the medical access device using the squeegee tip and causing the excess fluid to be trapped in the medical connector by the retractable seal.

12. The method of claim 11 wherein the retractable seal is part of a flexible sleeve surrounding the male luer portion of the connector and fixed to an end of the male luer portion distal from the at least one outlet port and the excess fluid is trapped between the flexible sleeve and the male luer portion.

* * * * *